United States Patent [19]

Davidson

[11] Patent Number: 5,713,947
[45] Date of Patent: Feb. 3, 1998

[54] CARDIOVASCULAR IMPLANTS OF ENHANCED BIOCOMPATIBILITY

[75] Inventor: James A. Davidson, Germantown, Tenn.

[73] Assignee: Smith & Nephew, Inc., Memphis, Tenn.

[21] Appl. No.: 470,251

[22] Filed: Jun. 6, 1995

Related U.S. Application Data

[60] Division of Ser. No. 112,599, Aug. 26, 1993, Pat. No. 5,477,864, which is a continuation-in-part of Ser. No. 36,414, Mar. 24, 1993, Pat. No. 5,509,933, which is a continuation-in-part of Ser. No. 986,280, Dec. 7, 1992, abandoned, which is a continuation-in-part of Ser. No. 647,453, Jan. 28, 1991, Pat. No. 5,169,597, which is a continuation of Ser. No. 454,181, Dec. 21, 1989, abandoned.

[51] Int. Cl.$^6$ .................................................. A61F 2/06
[52] U.S. Cl. .................. 623/1; 623/2; 623/3; 623/11; 623/66
[58] Field of Search ............................. 623/2, 3, 11, 16, 623/18, 20, 22, 23, 66, 900; 606/53, 69, 76; 148/316, 317, 421, 669

[56] References Cited

U.S. PATENT DOCUMENTS

| | | |
|---|---|---|
| 2,892,706 | 6/1959 | Jafee et al. . |
| 2,987,352 | 6/1961 | Watson . |
| 3,370,946 | 2/1968 | Bertea et al. . |
| 3,408,604 | 10/1968 | Doi et al. ................................. 335/216 |
| 3,643,658 | 2/1972 | Steinemann . |
| 3,677,795 | 7/1972 | Bokros et al. . |
| 3,685,059 | 8/1972 | Bokros et al. ............................ 623/2 |
| 3,752,664 | 8/1973 | Steinemann ............................. 420/417 |
| 3,777,346 | 12/1973 | Steinemann . |
| 3,849,124 | 11/1974 | Villant ...................................... 420/417 |
| 3,867,209 | 2/1975 | Horiuchi et al. ......................... 148/96 |
| 3,906,550 | 9/1975 | Rostoker et al. ....................... 3/1.921 |
| 3,911,783 | 10/1975 | Gapp et al. .............................. 420/417 |
| 3,969,130 | 7/1976 | Bokros et al. ........................... 427/332 |
| 4,040,129 | 8/1977 | Steinemann et al. .................. 148/11.5 |
| 4,145,764 | 3/1979 | Suzuki et al. . |
| 4,170,990 | 10/1979 | Baumgart et al. ...................... 606/78 |
| 4,197,643 | 4/1980 | Burstone et al. ....................... 420/421 |
| 4,511,411 | 4/1985 | Brunner et al. . |
| 4,857,269 | 8/1989 | Wang et al. ............................. 420/417 |
| 4,902,359 | 2/1990 | Takeuchi et al. ....................... 148/133 |
| 4,983,184 | 1/1991 | Steinemann ............................. 623/66 |
| 5,169,597 | 12/1992 | Davidson et al. ....................... 428/613 |

FOREIGN PATENT DOCUMENTS

| | | |
|---|---|---|
| 0 437 079 A1 | 12/1990 | European Pat. Off. . |
| 2703529 | 8/1978 | Germany . |

OTHER PUBLICATIONS

Zwicker, et al., Z. Metallkunde, 61 (1970) pp. 836–847.

Collings, E.W., "The Physical Metallurgy of Titanium Alloys," *American Society For Metals*, pp. 40–41, 66–69, 72–73, 120–121, 190–191, 194–195, 214–215, 218–219, 226–227 (No Date).

(List continued on next page.)

*Primary Examiner*—John G. Weiss
*Assistant Examiner*—Francis K. Cuddihy
*Attorney, Agent, or Firm*—Pravel, Hewitt, Kimball & Krieger

[57] ABSTRACT

Cardiovascular and other medical implants fabricated from low-modulus Ti—Nb—Zr alloys to provide enhanced biocompatibility and hemocompatibility. The cardiovascular implants may be surface hardened by oxygen or nitrogen diffusion or by coating with a tightly adherent, hard, wear-resistant, hemocompatible ceramic coating. The cardiovascular implants include heart valves, total artificial heart implants, ventricular assist devices, vascular grafts, stents, electrical signal carrying devices such as pacemaker and neurological leads, defibrillator leads, and the like. It is contemplated that the Ti—Nb—Zr alloy can be substituted as a fabrication material for any cardiovascular implant that either comes into contact with blood thereby demanding high levels of hemocompatibility, or that is subject to microfretting, corrosion, or other wear and so that a low modulus metal with a corrosion-resistant, hardened surface would be desirable.

17 Claims, 7 Drawing Sheets

OTHER PUBLICATIONS

Collings, E.W., "The Physical Metallurgy of Titanium Alloys," *American Society for metals* pp. 68–70 (No Date).

Albert, et al., Z. Metallunde, 62 (1972) 126.

Brown & Merritt, "Evaluation of Corrosion Resistance of Biology," Case Western Reserve University, 13 Feb. 1986 (1:8).

Mears, "Electron–Probe Microanalysis of Tissue and Cells From Implant Areas," *JNL of Bone and Joint Surgery*, vol. 48B, No. 3, pp. 576–676 (Aug. 1966).

Ferguson, Laing, and Hodge, "The Ionization of Metal Implants in Living Tissues," *JNL of Bone and Joint Surgery*, vol. 42A, No. 1, pp. 77–90 (Jan. 1960).

Hoar and Mears, "Correction–Resistant Alloys in Chloride Solutions Materials for Surgical Implants," pp. 506–507.

Kirk–Othmer Encyclopedia of Chemical Technology, vol. 23, pp. 98–113.

Jepson, et al., The Science & Tech., Titanium Ed. Jaffee, et al., Pergamon, N.Y., 1968.

Heller, et al., Journ. Less Common Metals, 24 (1971) 265.

Van Noort, R., Jour. Mat. Sci., 22 (1987) 3801.

The Japan Medical Review, vol. 12, (Undated) unnumbered page, pp. 12 , 23

Author Unknown, "Titanium–Niobium Base Quaternary Alloys," (Date Unknown), pp. 405–419.

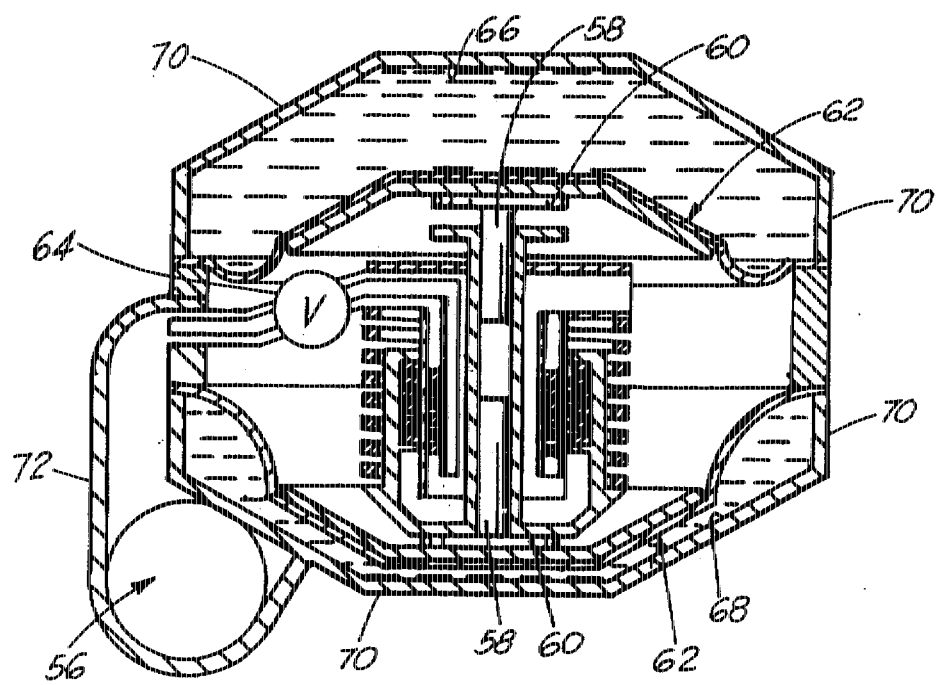
FIG. 7
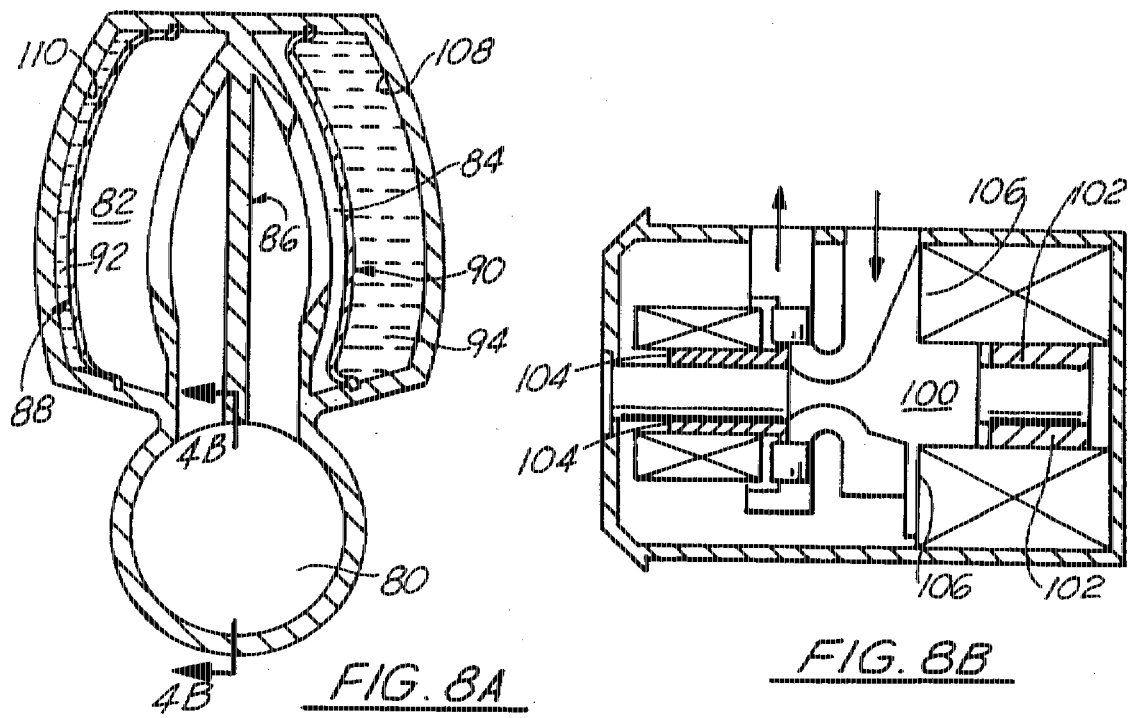
FIG. 8A
FIG. 8B

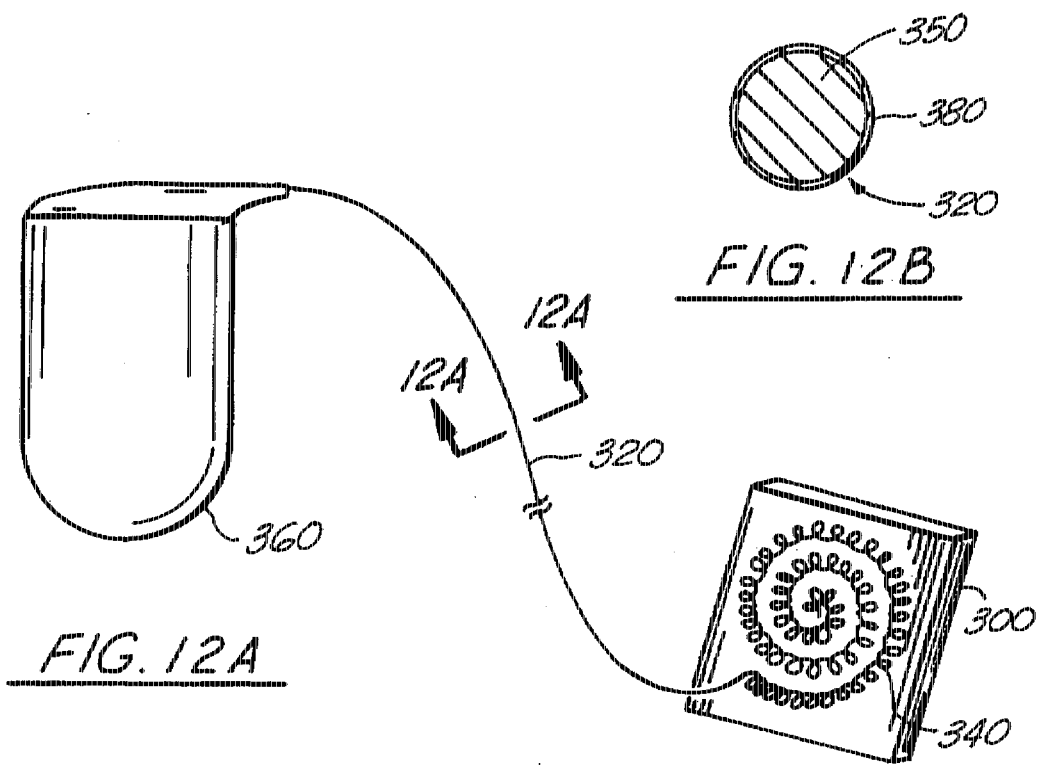
FIG. 12B
FIG. 12A
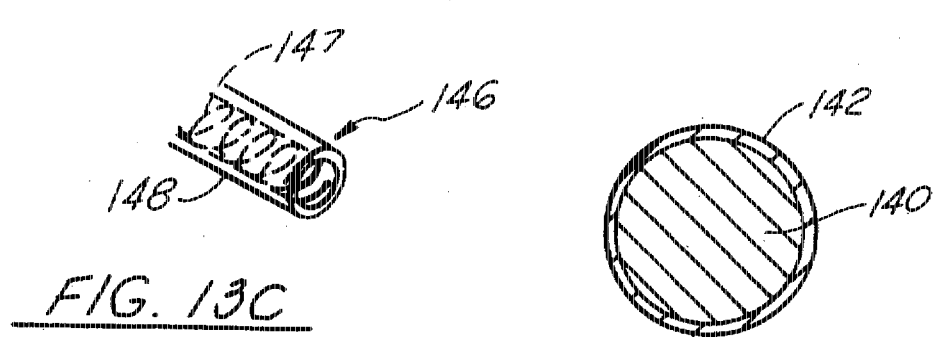
FIG. 13C
FIG. 13A
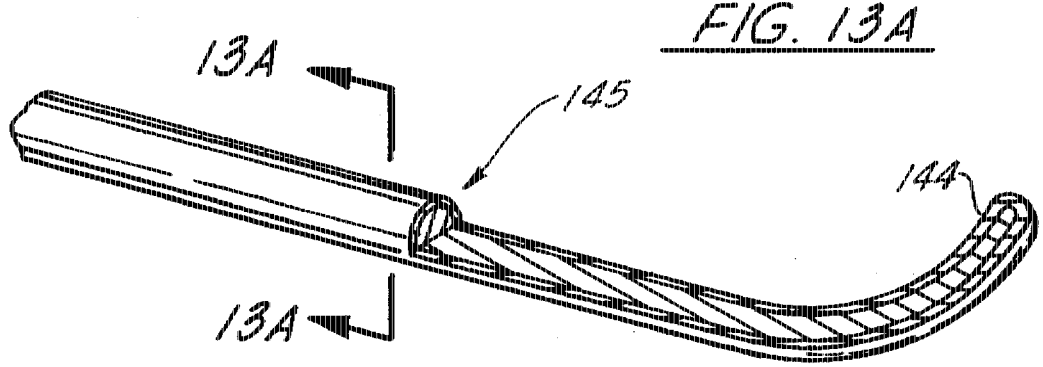
FIG. 13B

CARDIOVASCULAR IMPLANTS OF ENHANCED BIOCOMPATIBILITY

RELATED APPLICATIONS

This is a division of application Ser. No. 08/112,599 filed on Aug. 26, 1993, issued as U.S. Pat. No. 5,477,864 which is a continuation-in-part of U.S. Ser. No. 08/036,414 filed on Mar. 24, 1993, issued U.S. Pat. No. 5,509,933 which is in turn a continuation-in-part of U.S. Ser. No. 07/986,280, filed on Dec. 7, 1992, abandoned, which is a continuation-in-part of Ser. No. 07/647,453, filed on Jan. 28, 1991, issued as U.S. Pat. No. 5,169,597, which is in turn a continuation of U.S. Ser. No. 07/454,181, filed on Dec. 21, 1989, abandoned.

BACKGROUND OF THE INVENTION

1. Field of the Invention

This invention relates to a range of cardiovascular and other implants fabricated of metallic alloys of enhanced hemocompatibility that can optionally be surface hardened to provide resistance to wear, or cold-worked or cold-drawn to reduce elastic modulus, if necessary. More specifically, the invention is of synthetic heart valves, ventricular assist devices, total artificial hearts, stents, grafts, pacers, pacemaker leads and other electrical leads and sensors, defibrillators, guide wires and catheters, and percutaneous devices fabricated of Ti—Nb—Zr alloys.

2. Description of the Related Art

Cardiovascular implants have unique blood biocompatibility requirements to ensure that the device is not rejected (as in the case of natural tissue materials for heart valves and grafts for heart transplants) or that adverse thrombogenic (clotting) or hemodynamic (blood flow) responses are avoided.

Cardiovascular implants, such as heart valves, can be fabricated from natural tissue. These bioprostheses can be affected by gradual calcification leading to the eventual stiffening and tearing of the implant.

Non-bioprosthetic implants are fabricated from materials such as pyrolytic carbon-coated graphite, pyrolytic carbon-coated titanium, stainless steel, cobalt-chrome alloys, cobalt-nickel alloys, alumina coated with polypropylene and poly-4-fluoroethylene.

For synthetic mechanical cardiovascular devices, properties such as the surface finish, flow characteristics, surface structure, charge, wear, and mechanical integrity all play a role in the ultimate success of the device. For example, typical materials used for balls and discs for heart valves include nylon, silicone, hollow titanium, TEFLON™, polyacetal, graphite, and pyrolytic carbon. Artificial hearts and ventricular assist devices are fabricated from various combinations of stainless steel, cobalt alloy, titanium, Ti—6Al—4V alloy, carbon fiber reinforced composites, polyurethanes, BIOLON™ (DuPont), HEMOTHANE™ (Sarns/3M), DACRON™, polysulfone, and other thermoplastics. Pacers, defibrillators, leads, and other similar cardiovascular implants are made of Ni—Co—Cr alloy, Co—Cr—Mo alloy, titanium, and Ti—6Al—4V alloy, stainless steel, and various biocompatible polymers. Stents and vascular grafts are often made of DACRON™ stainless steel or other polymers. Catheters and guide wires are constructed from Co—Ni or stainless steel wire with surrounding polymer walls.

One of the most significant problems encountered in heart valves, artificial hearts, assist devices, pacers, leads, stents, and other cardiovascular implants is the formation of blood clots (thrombogenesis). Protein coatings are sometimes employed to reduce the risk of blood clot formation. Heparin is also used as an anti-thrombogenic coating.

It has been found that stagnant flow regions in the devices or non-optimal materials contribute to the formation of blood clots. These stagnant regions can be minimized by optimizing surface smoothness and minimizing abrupt changes in the size of the cross section through which the blood flows or minimizing other flow interference aspects. While materials selection for synthetic heart valves, and cardiovascular implants generally, is therefore dictated by a requirement for blood compatibility to avoid the formation of blood clots (thrombus), cardiovascular implants must also be designed to optimize blood flow and wear resistance.

Even beyond the limitations on materials imposed by the requirements of blood biocompatibility and limitations to designs imposed by the need to optimize blood flow, there is a need for durable designs since it is highly desirable to avoid the risk of a second surgical procedure to implant cardiovascular devices. Further, a catastrophic failure of an implanted device will almost certainly result in the death of the patient.

The most popular current heart valve designs include the St. Jude medical tilting disc double cusp (hi-leaf) valve. This valve includes a circular ring-like pyrolytic carbon valve housing or frame and a flow control element which includes pyrolytic carbon half-discs or leaves that pivot inside the housing to open and close the valve. The two leaves have a low profile and open to 85° from the horizontal axis.

Another popular heart valve is the Medtronic-Hall Valve wherein the flow control element is a single tilting disc made of carbon coated with pyrolytic carbon which pivots over a central strut inside a solid titanium ring-like housing. A third, less popular design, is the Omniscience valve which has a single pyrolytic disc as a flow control element inside a titanium housing. Finally, the Starr-Edwards ball and cage valves have a silastic ball riding inside a cobalt-chrome alloy cage. The cage is affixed to one side of a ring-like body for attachment to the heart tissue. More recent designs include trileaflet designs and concave bileaflet designs to improve blood flow.

From the point of view of durability, heart valves made of low-thrombogenic pyrolyte carbon could fail from disc or pivot joint wear or fracture related to uneven pyrolytic carbon coating, fracture of the ball cage, disc impingement, strut wear, disc wear, hinge failure, and weld failure. A more recent heart valve, the Baruah Bileaflet is similar to the St. Jude design but opens to 80° and is made of zirconium metal. The valve has worked well over its approximately two-year history with roughly 200 implants to date in India. This performance can be partly attributed to the lower elastic modulus of zirconium( about 90 GPa) and the resultant lower contact stress severity factor (Cc of about $0.28 \times 10^{-7}$m) when the disc contacts the frame. In contrast, pyrolytic constructions produce contact stress severity factors of about $0.54 \times 10^{-7}$m.

Although zirconium has worked well to date and can reduce contact stress severity, zirconium metal is relatively soft and sensitive to fretting wear. This is partly due to hard, loosely attached, naturally-present passive oxide surface films (several nanometers in thickness) which can initiate microabrasion and wear of the softer underlying metal. However, this naturally present zirconium oxide passive film is thrombogenically compatible with blood and the design is acceptable from a hemodynamic standpoint. Therefore, while the zirconium bileaflet valve appears to meet at least two of the major requirements for cardiac valve implants, namely blood compatibility and design for minimum stagnant flow regions, the use of soft zirconium metal leads to a relatively high rate of fretting wear and leads to the expectation that the valve may be less durable than one produced from materials less susceptible to fretting wear. Titanium and titanium alloys present a similar limitation, and Co—Cr—Mo, stainless steel, and Co—Ni alloys have much greater elastic modulus.

There exists a need for a metallic cardiac valve implant that is biocompatible, compatible with blood in that it does not induce blood clotting and does not form a calcified scale, that is designed to minimize stagnant flow areas where blood clotting can be initiated, that has a low elastic modulus for lower contact stress severity factors to ensure resistance to wear from impact, and that has a surface that is also resistant to microabrasion thereby enhancing durability.

Heart diseases, many of which cannot be cured by conventional surgery or drug therapy, continue to be a leading cause of death. For the seriously ill patient, heart replacement is often one of the few viable options available.

In 1988, the NHBLI began funding research and development for permanently implantable, electrically driven, total artificial hearts (TAHs). The pumping mechanism of the TAHs would be implanted into the chest cavity of the patient and the device would be powered by a battery pack and a small transformer, worn by the patient, which transmits energy to the heart with no physical connections through the skin. The NHBLI funded four separate groups: The Cleveland Clinic Foundation & Nimbus, Inc.; Pennsylvania State University & Sarns/3M; The Texas Heart Institute and Abiomed, Inc.; and the University of Utah. Consequently, four competing designs were developed.

The development of TAHs posed several issues. Firstly, it was necessary to duplicate the action of a human heart, ensure long-term reliability and biocompatibility, while producing a device that fits into the chest cavity in terms of both its total volume and the orientation of its connections to natural vessels in the body. Aside from the purely mechanical, wear, and power supply issues, it is also necessary that the design and materials prevent infection and thrombosis. Blood is a non-Newtonian fluid and its properties, such as viscosity, change with oxygen content, kidney function, and even the age of the patient. Further, plasma contains a suspension of fragile red blood cells which may be caught in artificial valves, or other mechanically stressful areas, thereby destroying these cells. It is therefore necessary to develop a TAH that does not stress blood components, and to fabricate the pump from materials that are not only biocompatible, but also "blood compatible" in the sense of minimizing damage to blood components and minimizing the formation of blood clots.

Many of the above comments also apply to ventricular assist devices (VADs), one of which is being developed by the Novacor Division of Baxter Health Care Corp. In the use of a VAD, the patient's heart remains in place while the VAD boosts the pumping pressure of the left ventricle of the heart. Consequently, the VAD is an assist device rather than a replacement. However, the VAD must be blood compatible for the same reasons as the total artificial heart.

There exists a need for a material that is lightweight, readily formable into complex shapes, biocompatible, and blood and tissue compatible with a hard surface that is resistant to abrasive wear, microfretting wear, and the corrosive effects of body fluids, for use in heart assist or replacement devices (including EMHs, VADs, and TAHs) to prolong the life of mechanical components while at the same time minimizing any deleterious effect on blood components.

SUMMARY OF THE INVENTION

The invention provides cardiovascular and other medical implants of a low modulus, biocompatible, hemocompatible, metallic alloy of titanium with niobium and optionally zirconium. The invention implants include heart valves, artificial hearts, ventricular assist devices, defibrillators, pacers, electrical leads, sensors, grafts, stents, and catheter devices. The invention also provides surface hardened versions of these devices produced by oxygen or nitrogen diffusion hardening to improve resistance to cavitation, microfretting wear, and impact-induced wear.

The inherently low modulus of Ti—Nb—Zr alloys, between about 6 to about 12 million psi depending on metallurgical treatment and composition, provide a more flexible and forgiving construct for cardiovascular applications while improving contact stress levels, valve closure, and the ability of leaves in certain valve designs to self-align with blood flow and reduce thrombodynamic effects.

The invention provides components for use in mechanical heart replacement or assist devices, such as external mechanical hearts (EMHs), total artificial hearts (TAHs), and ventricular assist devices (VADs), that are lightweight, while also being resistant to corrosive body fluids, mechanical wear, abrasive wear, and microfretting wear. Further, the components have much improved blood compatibility in the sense of reduced risk of thrombogenesis (blood clotting).

The preferred low modulus titanium alloys of the invention have the compositions: (i) titanium; about 10 wt. % to about 20 wt. % niobium; and optionally from about 0 wt. % to about 20 wt. % zirconium; and (ii) titanium; about 35 wt. % to about 50 wt. % niobium; and optionally from about 0 wt. % to about 20 wt. % zirconium. Tantalum can also be present as a substitute for Nb. These alloys are referred to herein as "Ti—Nb—Zr alloys," even though tantalum may also be present.

The exclusion of elements besides titanium, zirconium, and niobium, or tantalum results in an alloy which does not contain known toxins or carcinogens, or elements that are known or suspected of inducing diseases or adverse tissue response in the long term.

Without the presence of zirconium in the composition, the ability of the Ti—Nb—Zr alloy to surface harden during oxygen or nitrogen diffusion hardening treatments is more limited. Therefore, presence of zirconium is especially preferred when the alloy implant must be diffusion hardened. Other non-toxic filler materials such as tantalum, which stabilize the β-phase of titanium alloy, but do not affect the low modulus, i.e., maintain it at less than about 85 GPa, could also be added.

A porous coating, such as plasma-sprayed or sintered titanium or titanium alloy (including Ti—Nb—Zr alloy) beads or wire mesh may also be added to the implant's surfaces to improve tissue attachment, such as the formation of an endothelial cell layer, preferred in artificial heart, ventricular assist devices, grafts, and stent devices. Such coatings provide more favorable blood interaction and flow characteristics, and also tend to stabilize the implant with the body. Thus, such porous coatings may also be useful for connecting regions of these devices as well as for heart valves and grafts. Even though the application of such porous coatings usually requires sintering at relatively high temperatures, the properties of the Ti—Nb—Zr alloy that might affect its usefulness as an implant material are not adversely affected.

BRIEF DESCRIPTION OF THE DRAWINGS

A better understanding of the present invention can be obtained when the following detailed description of the preferred embodiments is considered in conjunction with the following drawings, in which:

FIG. 7 is a schematic diagram of the Cleveland Clinic/Nimbus, Inc. total artificial heart.

FIG. 8A is a schematic diagram, in cross section, of the Texas Heart Institute/Abiomed total artificial heart.

FIG. 8B is a side view, in cross section, of the Texas Heart Institute/Abiomed total artificial heart of FIG. 8A.

FIG. 12A is a schematic diagram of the components of a defibrillator, showing power source, lead wire, and polymeric patch with coiled electrode.

FIG. 12B is a cross section of the lead wire of FIG. 12A.

FIG. 13A is a schematic diagram, in partial cross section, of the distal end of a guide wire.

FIG. 13B is a cross-section of the guide wire with coating thickness exaggerated.

FIG. 13C shows a catheter containing coiled wire and polymer wall.

DETAILED DESCRIPTION OF THE PREFERRED EMBODIMENTS

Figure 1:
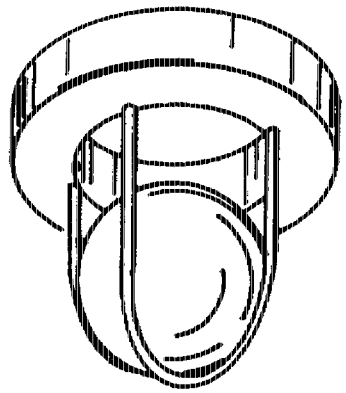
FIG. 1 shows a simplified representation of a ball valve, like the Starr-Edwards Valve.
Figure 2:
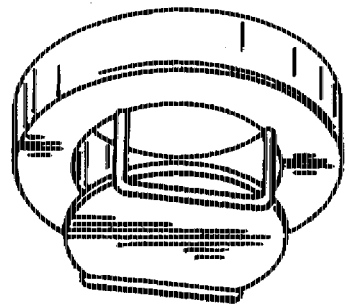
FIG. 2 is a simplified representation of a disc valve.
Figure 3:
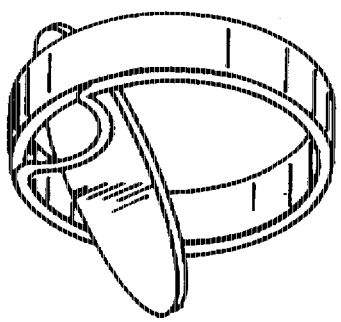
FIG. 3 is a simplified representation of a tilting disc, single cusp valve like the Medtronic-Hall valve.

The implants of the invention are fabricated from an alloy containing titanium as a component. The preferred low modulus titanium alloys have the compositions: (i) titanium, about 10 wt. % to about 20 wt. % niobium, and optionally from about 0 wt. % to about 20 wt. % zirconium; and (ii) titanium, about 35 wt. % to about 50 wt. % niobium, and optionally from about 0 wt. % to about 20 wt. % zirconium.

In a preferred embodiment wherein the implants are surface hardened by oxygen or nitrogen diffusion, zirconium is beneficially present in amounts ranging from about 0.5 to about 20 wt. %.

Even though it is apparent that the titanium proportion of alloy used to make the invention implants could be less than 50 wt. %, nevertheless, for the purposes of this specification, it is referred to as a "Ti—Nb—Zr alloy" or a "titanium alloy." The alloy most preferably comprises about 74 wt. % titanium in combination with about 13 wt. % of zirconium and 13 wt. % of niobium. While tantalum may be substituted for niobium to stabilize β-phase titanium, niobium is the preferred component due to its effect of lowering the elastic modulus of the alloy when present in certain specific proportions. Other elements are not deliberately added to the alloy but may be present in such quantities that occur as impurities in the commercially pure titanium, zirconium, niobium, or tantalum used to prepare the alloy and such contaminants as may arise from the alloying process.

In the specification and claims, the term "high strength" refers to an alloy having a tensile strength above at least about 620 MPa.

The term "low modulus," as used in the specification and claims, refers to a Young's modulus below about 90 GPa.

Although the hot rolled, reheated, and quenched Ti—Nb—Zr alloy is a suitable implant material, its properties can be improved by forging or other metallurgical processes or an aging heat treatment or a combination of these. Aging treatment can increase the strength and hardness of the material, and reduce its elongation while maintaining a relatively low modulus of elasticity. The treatment can be varied to obtain the desired properties. U.S. Pat. No. 5,169,597 to Davidson, et al., hereby fully incorporated by reference, deals in more detail with the useful Ti—Nb—Zr alloys. Further, U.S. Ser. No. 08/036,414, hereby fully incorporated by reference, teaches how to hot work Ti—Nb—Zr alloys to produce high strength, low modulus medical implants.

It may be desirable for other reasons, such as reducing microfretting wear between mating mechanical components, to surface harden the alloy implants using oxygen or nitrogen diffusion hardening methods, or coating with a hard wear resistant coating. In the latter event, the surface of the prosthesis may be coated with an amorphous diamond-like carbon coating or ceramic-like coating such as zirconium or titanium oxide, zirconium or titanium nitride, or zirconium or titanium carbide using chemical or plasma vapor deposition techniques to provide a hard, impervious, smooth surface coating. These coatings are especially useful if the prosthesis is subjected to conditions of wear, such as, for instance, in the case of mating parts in artificial hearts or ventricular assist devices, or as an electrically insulative coating on electrical leads (i.e., pacemaker, defibrillator, neurological, sensors) of Ti—Nb—Zr alloy.

Methods for providing hard, low-friction, impervious, biocompatible amorphous diamond-like carbon coatings are known in the art and are disclosed in, for example, EPO patent application 302 717 A1 to Ion Tech and Chemical Abstract 43655P, Vol. 101, describing Japan Kokai 59/851 to Sumitomo Electric, all of which are incorporated by reference herein as though fully set forth.

A preferred process for oxygen diffusion hardening is described in our co-pending patent application U.S. Ser. No. 08/112,612 (temporarily identified by Attorney Docket No. A93096US), now U.S. Pat. No. 5,372,660 filed on the same day as this patent application, which is hereby fully incorporated by reference. Oxygen diffusion hardening according to this process requires the supply of oxygen, or an oxygen containing atmosphere, or compounds partially composed of oxygen, such as water (steam), carbon dioxide, nitrogen dioxide, sulfur dioxide, and the like. These substances are supplied to the implant to be hardened which is maintained at a temperature preferably between 200° C. and 1200° C. The amount of time required at a given temperature to effectively produce the surface and near-surface hardened implants is related exponentially, by an Arhennius-type relationship to the temperature. That is, shorter periods of time-are required at higher temperatures for effective diffusion hardening. The resultant oxygen diffusion hardened implants are characterized in that the oxide film contains primarily a mixture of titanium and zirconium oxides in the implant surface. Niobium oxides may also be present. Immediately underlying this mixed-oxide film is sometimes a region of oxygen-rich metal alloy. Underlying the sometimes-obtained oxygen-rich alloy layer is the core Ti—Ni—Zr alloy. The interface between the sometimes-obtained oxygen-rich alloy layer and the oxide regions is typically zirconium-rich in comparison to the underlying Ti—Ni—Zr alloy. In a most preferred embodiment, the Ti—Ni—Zr alloy is subjected to temperature and an environment of argon gas that has been moisturized by bubbling through a water bath. The water vapor disassociates at the implant surface to produce oxygen which diffuses into the implant to produce the desired hardened surface.

Nitrogen diffusion processes can also be utilized in which nitrogen sources are provided instead of oxygen. These nitrogen diffusion surface hardening processes will tend to harden the metal alloy substrate in a similar manner to that of oxygen diffusion hardening or conventional oxygen hardening (which is also useful), and produce a yellow-orange insulative, wear-resistant surface oxide instead of the blue-black surface oxide which typically forms from the in situ oxygen diffusion hardening process.

Implants fabricated from the inventive alloy may be supplied with a porous bead or wire coating of titanium alloy of the same or different composition including pure titanium to allow endothelial cell attachment to blood-contacting flow surfaces or for stabilization of the implant in the body of the patient after implantation by tissue ingrowth into the porous structure. Such porous structures are normally attached to the implant surface by sintering or plasma spraying. Sintering involves heating the implant to above about 1250° C. The mechanical properties of titanium alloys can change significantly due to substantial grain growth and other metallurgical factors arising from the sintering process. Thus, after sintering to attach the porous coating, it may be desirable in some instances to reheat the Ti—Nb—Zr implant, for example, to about 875° C. (or above the β-transus) for 20–40 minutes then water quench before aging at about 500° C. for about 6 hours to restore mechanical properties. If quenched adequately from the sintering temperature, it may be possible to go directly to the aging process. An alternative method of attaching a porous coating is to simply plasma spray metal powder or micro-beads onto the implant's surface after appropriate mechanical and thermal treatments.

Further, the implants of the invention may optionally be surface coated with medicaments such as anti-inflammatory agents, anti-thrombus agents, antibiotics, proteins that reduce platelet adhesion, and the like to improve their acceptability in a living body.

Heart Valves

Figure 4:
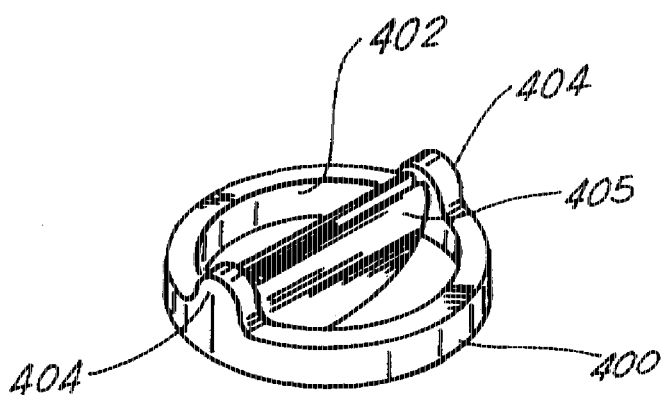
FIG. 4 is a simplified representation of a tilting disc, double cusp or bileaflet valve of the St. Jude or Baruah type.

In its simplest form, a synthetic cardiac valve includes a valve body for affixing the valve to the body tissue and through which blood flows, and a flow control element for allowing or blocking off blood flow. For instance, FIG. 4 shows a typical bileaflet valve having a valve body that includes a ring-like housing 400 with an inner ring 402 that has two flanges 404 each containing two slots for receiving hinges attached to leaflets. The flow control element of this valve comprises two leaflets 405, in the approximate shape of half discs, with hinge elements attached at diametrically opposite ends. These hinge elements fit within apertures or slots in the flanges 404 of the inner ring 402 and are able to rotate through less than 180° C. in these apertures. Thus, in operation, the flow control elements are in the position shown in FIG. 4 with the valve open with blood flowing from top to bottom. When blood flow reverses and flows from bottom to top, the bileaflets 405 pivot about their hinges to close the apertures in the ring-like valve body. Consequently, there is a significant amount of movement about the hinge elements and slots where microfretting wear might be initiated. Furthermore, the bileaflet half disc flow control elements 405 may impinge upon the inner ring 402 of the valve body, thereby leading to cavitation or impact-induced wear.

The invention provides heart valves of various designs, exemplified in FIG. 1–4, each comprising parts subject to impact and wear that are fabricated from Ti—Nb—Zr alloy. More recent designs (not shown in the Figures) include concave bileaflet and trileaflet designs which are intended to improve blood flow. The heart valves are preferably subjected to a hardening process, such as oxygen or nitrogen diffusion hardening to produce a harder Ti—Nb—Zr surface that is resistant to microfretting wear at hinge points and impact wear at those locations where a flow control element impacts the valve body. Consequently, the invention valves have a longer cycle life than the currently used St. Jude, Omniscience, Starr-Edwards, Medtronic-Hall, or Baruah valves. Indeed, as mentioned before, the Baruah valve is currently fabricated of zirconium or zirconium alloys and would therefore be subject to relatively rapid wear because of the relative softness of zirconium and its alloys. The use of Ti—Nb—Zr alloy compositions also provides a low-thrombus, blood-compatible surface favorable in reducing the incidence of blood clots.

Artificial Hearts/Ventricular Assist Devices

Figure 5:
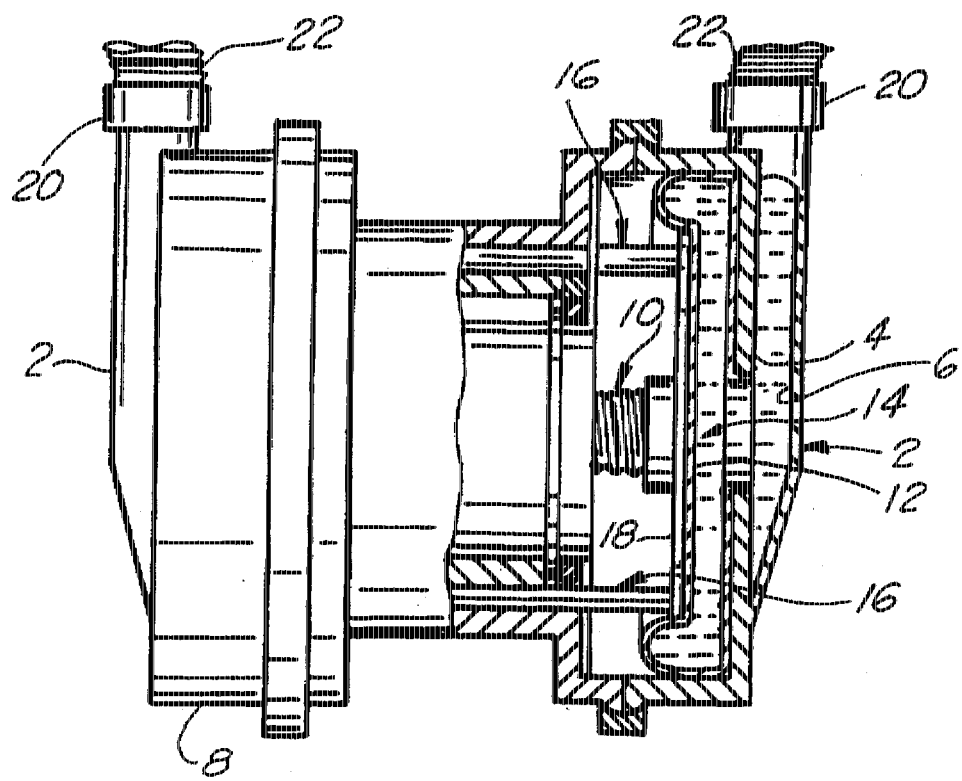
FIG. 5 is a schematic diagram of the Penn State/Sarns/3M design total artificial heart.

FIG. 5 is illustrative of the Penn State design which incorporates a stainless-steel roller screw 10 positioned between two flexible diaphragm blood pumps (right side pump 12 is shown, the other is within shell 8). A high speed, low torque brushless DC motor causes the roller screw 10 to turn thereby moving the roller screw shafts 16 linearly back and forth. To each end of the guide shaft 16 is attached a pusher plate 18. When the pusher plate 18 in the right side pump moves backward, blood is drawn into the pump space 14. At the same time, the pusher plate in the corresponding left side pump moves towards the left pushing blood out of its pump space. In this type of pump, the pusher plates 18 act against a flexible membrane 12, which is in contact with blood, and which can be inflated on the pump suction stroke and deflated on pump discharge stroke. The pusher plates are driven by the roller screw 10 and, thus, according to the invention, six revolutions of roller screw 10 are required for a full stroke with a motor speed of about 3,000 RPM. While planetary rollers are inserted between a roller screw nut and roller screw 10 to give rolling, not sliding contact and to spread mechanical load over many contact points, and while the entire roller screw system is hardened to minimize wear, the reliability of this system is improved by the use of the invention components. Thus, roller screw 10 and the roller-screw nut with which it is in rolling contact are both fabricated of Ti—Nb—Zr alloy and the surfaces are hardened or coated with a hard, tightly adherent coating. Further, the surfaces of the pump nozzles 2 shown as 4 and 6, connecting elements 20 and conduits 22, into and from which blood is continuously being pumped, is fabricated from Ti—Nb—Zr to reduce adverse reaction with blood tissue on those surfaces presented to blood components to minimize the potential for the formation of thrombus and blood clots.

Figure 6:
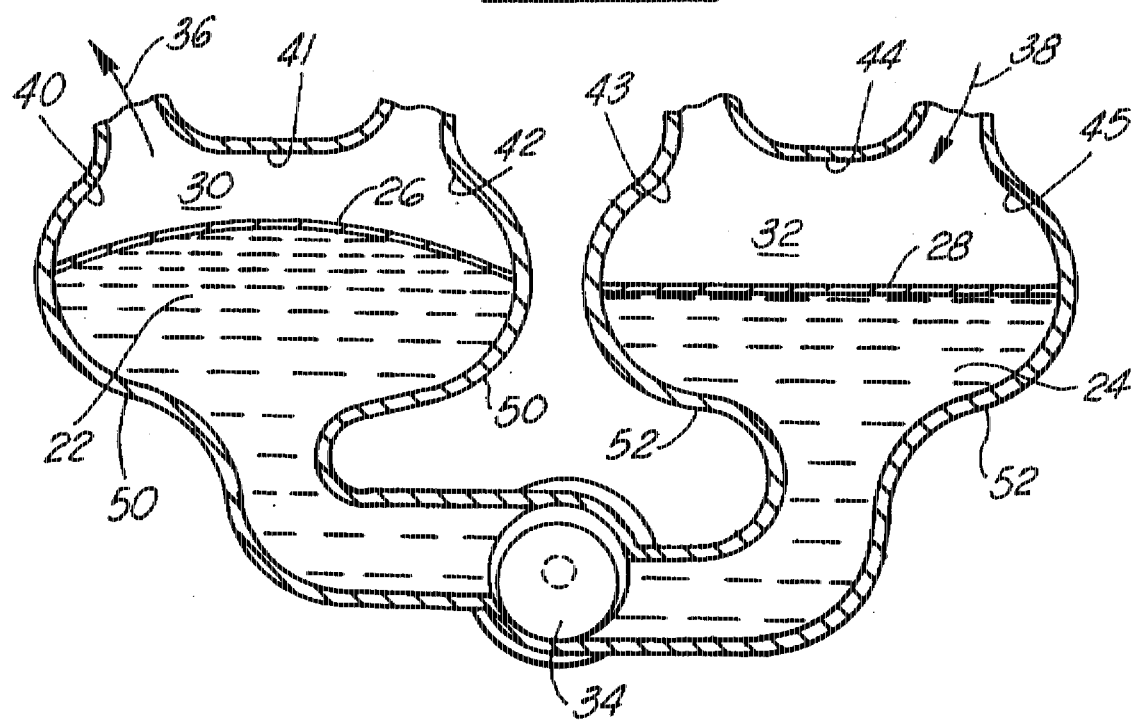
FIG. 6 is a schematic diagram of the University of Utah total artificial heart.

FIG. 6 is a schematic cross-sectional diagram of the University of Utah electrohydraulic heart. This heart includes shells 50 and 52 with a pump motor 34 interposed between them. In this type of heart, a motor 20 is used to pressurize silicone oil in regions 22 and 24 on the undersides of flexible diagrams 26 and 28, respectively, to move blood in and out of the chambers 30 and 32 above the flexible diaphragms. For example, when motor 34 pressurizes silicone oil into chamber 22, then flexible diaphragm 26 expands upward and outwardly to push blood flow out of chamber 30 in direction 36. At the same time, silicon oil flows out of chamber 24 towards chamber 22 thereby allowing flexible diaphragm 28 to assume a natural position, shown in FIG. 2, and drawing blood into chamber 32 as shown from direction 38. Upon reversal of the direction of the bidirectional pump 34, the opposite effects are achieved.

Since the University of Utah pump is of a bidirectional design, and typically operates at speeds between 10,000–13,000 RPM in the high pressure direction and 5,000–8,000 RPM in the reverse, moving components of the pump are subject to microfretting and mechanical wear. Therefore, the invention components for the bidirectional axial flow pump 34 used in the University of Utah TAH design are fabricated from Ti—Nb—Zr alloy coated hardened or with a wear resistant, hard coating that is tightly adherent, to reduce wear of the high speed components. Further, surfaces 40, 41, 42 43, 44 and 45 are in direct contact with blood and are made of Ti—Nb—Zr alloy to improve blood compatibility and reduce the potential for thrombus and blood clotting. Thus, the shells of the heart 50 and 52 are also fabricated of Ti—Nb—Zr alloy to reduce thrombogenesis.

FIG. 7 is a schematic cross-sectional illustration of the Cleveland Clinic TAH which utilizes a motor to turn a gear pump 56 which provides hydraulic pressure at about 100 psi to cause reciprocal movement of actuators 58 which in turn drive pusher-plates 60 that act on flexible diaphragms 62 to pump the blood. The actuators 58 operate slidingly within guide sleeve 64 so that wear on contact surfaces between actuator and sleeve may be expected. Further, the TAH has a flow reversing valve 64 with machine elements, such as bearing surfaces, subject to wear when the TAH is in use. Thus, TAH elements that are subject to wear and that may be advantageously fabricated of Ti—Nb—Zr alloys that are then surface hardened and/or coated with a hard, wear resistant, tightly adherent coating, include the guide sleeve 64, the actuators 58, the pump's gear elements and shaft and the rotary valve 64. Moreover, to reduce the risk of erosion damage to the pump from cavitation, the pump housing 72 may likewise be fabricated of Ti—Nb—Zr alloys. Finally, internal surfaces 66, 68 of the heart housing 70 are in direct blood contact. Thus it is desirable to fabricate housing 70 from Ti—Nb—Zr to reduce the risk of thrombogenesis.

FIGS. 8A and B are schematic diagrams of the Texas Heart Institute/Abiomed TAH design which utilizes a d.c. motor to drive a miniature centrifugal pump 80 that rotates at about 6,000–8,000 RPM. This pump 80 pressurizes hydraulic fluid alternately into chambers 82 and 84 separated by septum 86 and enclosed by flexible diaphragms 88 and 90 respectively. As fluid is pumped into chamber 82, diaphragm 88 expands into heart space 92 forcing blood from this space. At the same time, fluid is pumped from chamber 84 causing diaphragm 90 to relax and expanding heart space 94, drawing blood into the TAH. The hydraulic flow is reversed by a two-position 4-way rotating valve 100 of radial configuration for compactness. Rotary valve 100 rotates within sleeves 102 and 104 at high speed so that contacting-surfaces between the valve 100 and these sleeves are subject to wear. Further, rotary valve 100 rotates against seals 106 and wear may be expected at the contacting surfaces of the seals and the valve 100.

Several components of the Texas Heart Institute/Abiomed TAH may be fabricated according to the invention. Thus, high speed components of the centrifugal pump 80 subject to wear may be fabricated from Ti—Nb—Zr alloy and then surface hardened and/or coated with a tightly adherent, hard, wear resistant coating. Further, the rotary valve 100 itself and the surfaces of sleeves 102, 104 and seals 106 may be fabricated from Ti—Nb—Zr alloy then surface hardened or coated with an adherent, wear-resistant coating. Finally, the inner surfaces of the TAH 108, 110 may be fabricated from Ti—Nb—Zr alloys to improve blood compatibility and reduce the potential for thrombus and blood clotting.

Figure 9A:
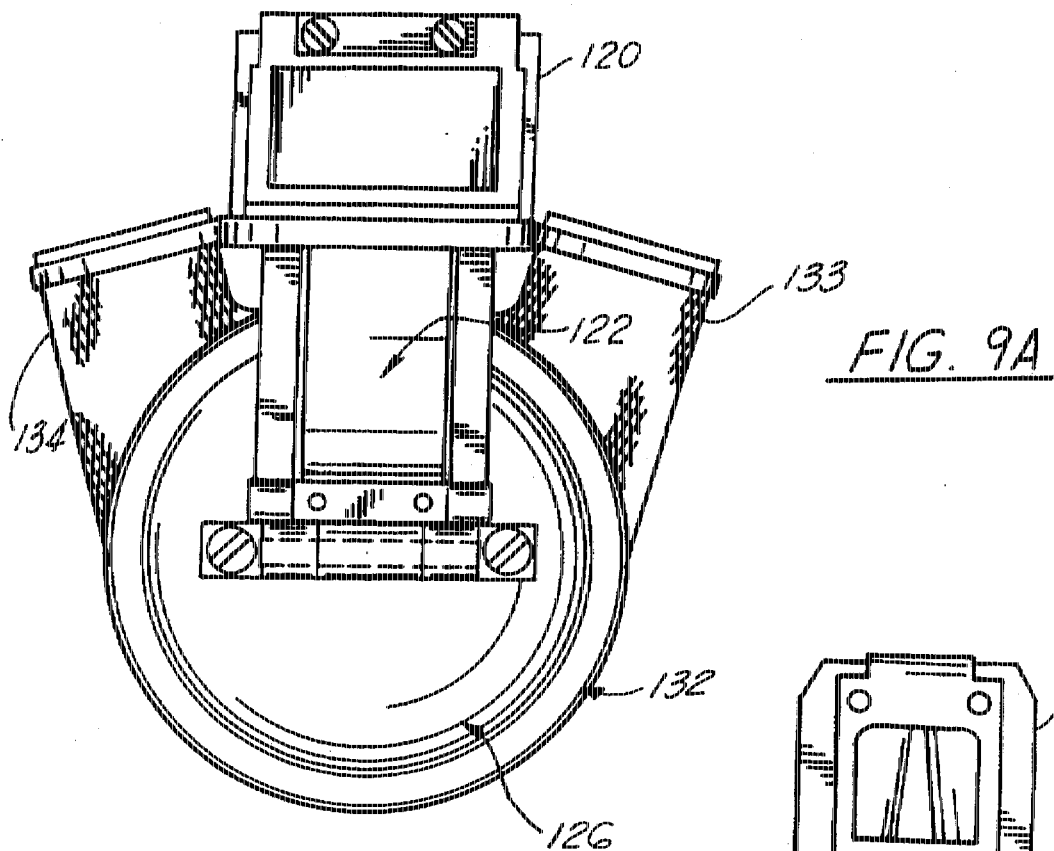
FIGS. 9A and B are schematic diagrams of end and front views, respectively, of a ventricular assist device.
Figure 9B:
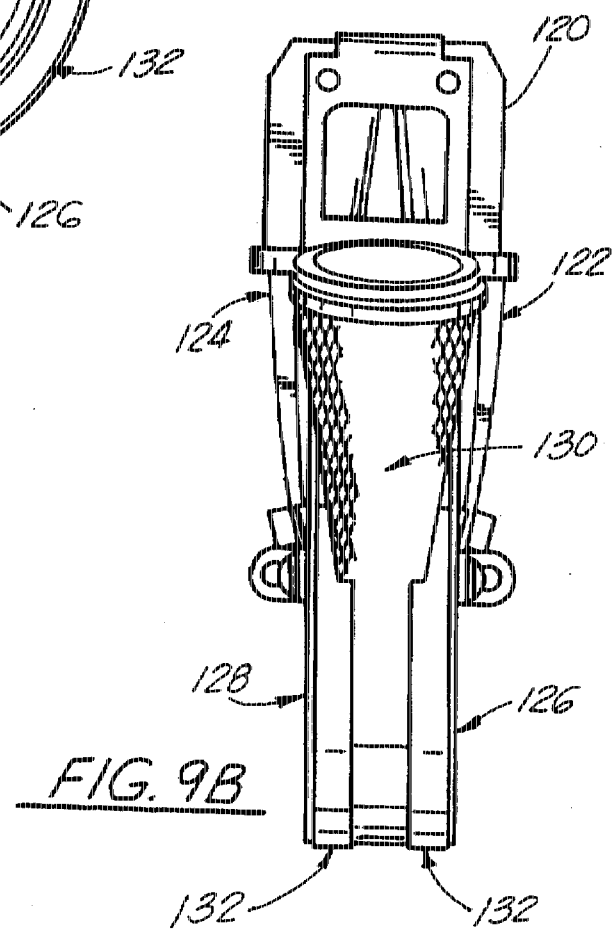

The Novacor designed VAD illustrated in FIGS. 9A and B have a solenoid mechanism 120 which sends energy through beam-springs 122, 124 that extend to the back of pump pusher plates 126, 128. The energy stored in the springs translates into linear motion of the plates which exerts force on the flexible blood sac 130. The blood sac 130 consists of a butyl rubber layer sandwiched between two layers of polyurethane Biomer. The blood sac 130 is supported within a cylindrical aluminum ring 132 that acts as a pump housing. The blood inflow 133 and outflow 134 ports are positioned tangentially on opposite sides of the housing to ensure straight-through blood flow. The ports are formed of an epoxy-impregnated Kevlar fabric shell that is integrated into the housing. The ports also encapsulate trileaflet inlet and outlet valves made from bovine pericardium tissue. When implanted into the body, fittings for attaching inflow and outflow valves to vascular conduits are bonded to a pump bulkhead, not shown, which also provides the framework for an encapsulating shell around the pump. This encapsulating shell also has provision for mounting the solenoid energy converter. The solenoid energy converter consists of two solenoid mechanisms, two lightweight titanium beam-springs, and an aluminum support structure. All of these metallic components would come into contact with blood components and body tissue. Therefore, the invention proposes that the titanium beam-springs be replaced with beam-springs of Ti—Nb—Zr alloy. Further, the aluminum support structure would likewise be replaced with a Ti—Nb—Zr alloy support structure that may optionally be hardened and/or coated with a hard coating.

Novacor has identified, in designing the solenoid, that "the challenge was coming up with something that would run for 100 million cycles a year, without requiring maintenance." O'Connor, Lee, "Novacor's VAD: How to Mend a Broken Heart," Mechan. Engr'g pp. 53–55 (November 1991). The invention components fabricated from Ti—Nb—Zr alloys then hardened or coated with hard, wear resistant coatings provide surfaces that are hard, microfretting wear resistant, biocompatible and blood compatible so that they would meet this goal. To further reduce friction and wear of wear surfaces of implant devices, a thin boron or silver surface layer can be applied as an overlay on the previously diffusion hardened Ti—Nb—Zr surface.

External mechanical hearts (EMHs) are used as a bridge to transplant. These hearts include the Jarvik-7 pneumatic heart and the more recent left-ventricular assist device, the Heartmate developed by Thermocardio Systems. In the Heartmate system, two tubes, one carrying air and the other electrical wire, pass from outside the body to an implanted blood pump. The pump is implanted in the abdomen and removes blood from the natural heart's left ventricle. This blood enters and exits the pump through 25 millimeter input and output valves made from chemically processed bovine tissue. The blood flows from the output valve through a dacron-wrapped polyurethane tube to the aorta. An electric motor mounted in the Heartmate's lower chamber actuates a flat-plate piston, which is bonded to a flexible polyurethane diaphragm. When the motor goes through one revolution, it turns a cam assembly that compresses the diaphragm, which pushes blood through the output valve. The operation of the pump is controlled by a microprocessor located in a shoulder bag which adjusts the heartbeat rate by changing the motor's current. According to the invention, the moving parts of the heartmate pump may be replaced with components fabricated from Ti—Nb—Zr alloys then hardened or coated with a hard coating to reduce mechanical wear, friction, and microfretting wear. Furthermore, those metallic components that come into contact with blood components, may also be replaced with Ti—Nb—Zr alloy components similarly coated to improve blood compatibility and reduce the risk of clot-formation.

The gravest problem in the use of the pneumatic Jarvik-7 heart has been identified as the formation of blood clots. O'Connor, Lee, "Engineering a Replacement for the Human Heart," Mechan. Engr'g pp. 36-43 (July 1991). In 1990, the FDA withdrew the Jarvik system from clinical trials due to concerns over quality control during manufacture. The University of Utah made modifications to the design of the Jarvik heart to develop a new system called the "Utah 100" which has elliptical pump housings, as opposed to the spherical housings of the Jarvik-7. Further, the Utah 100 has redesigned junctions for joining the diaphragms within the ventricles to the housing. These changes are said to have resulted in an about 70% reduction in blood clot formation relative to the Jarvik-7 design. However, according to the invention, yet further reduction in blood clot formation may be obtained by fabricating moving parts and those metallic surfaces that contact blood components from Ti—Nb—Zr alloys and then hardening and/or coating these components with hard, wear-resistant coating to increase blood compatibility and thrombus resistance, and to reduce abrasive wear, and reduce microfretting wear.

Guide Wires and Catheters

FIGS. 13A and B show, in partial cross section, the distal end of a guide wire fabricated according to the invention. The guide wire 145 has a core 140 of Ti—Nb—Zr alloy with a surface hardened coating 142 to reduce friction which may be further coated with a material that is bio- and hemocompatible and of low friction when in contact with the catheter wall or body tissue. The flexible catheter 146 through which the guide wire moves is also fabricated according to the invention and includes a coil 147 of low modulus titanium alloy which is generally encased by a polymer sheath 148 as shown schematically in FIG. 13C. The guide wire in this case is equipped with a cutting tip 144, preferably also made of Ti—Nb—Zr alloy with a diffusion hardened surface optionally with a hard ceramic or lubricating coating. Since the guide wire is fabricated of metal, it is highly visible under X-rays, providing excellent radiopacity. Boron or silver surface layers may also be deposited on the diffusion hardened surfaces to further reduce friction and wear.

Pacemakers and Electrical Signal Carrying Leads/Sensors

Pacemaker and other electronic leads are manufactured by several corporations, including Medtronic, which produces a range of pacemaker lead designs.

Figure 14A:
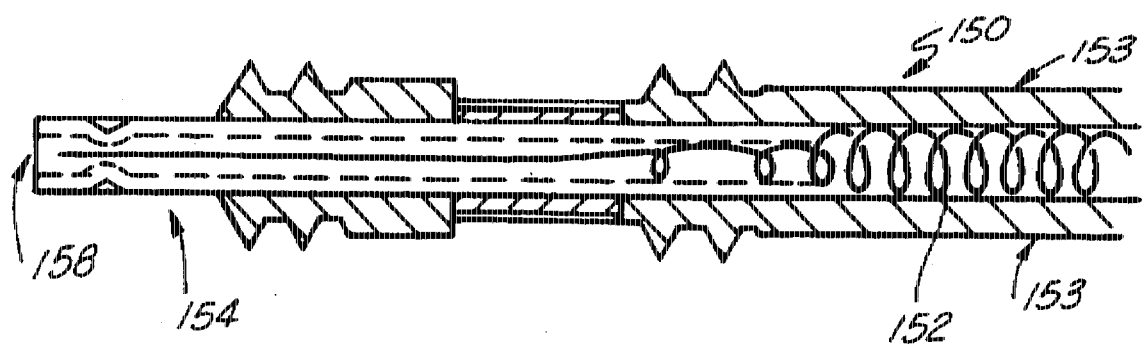
FIGS. 14A–C are schematic diagrams of prior art pacemaker leads with polyurethane covering.
Figure 14B:
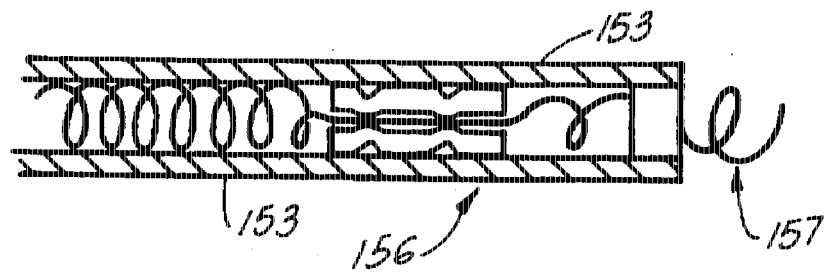
Figure 14C:
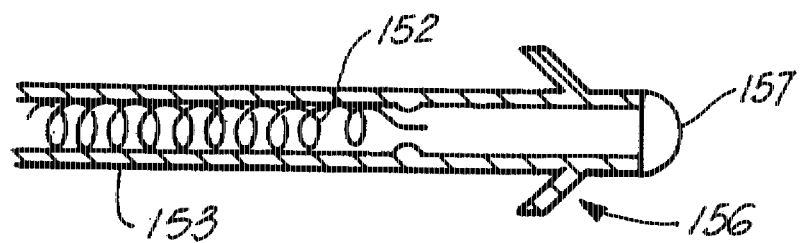
Figure 14D:
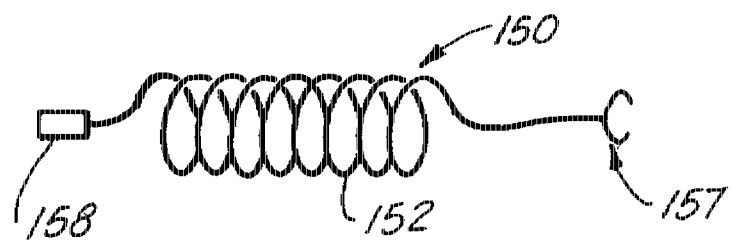
FIG. 14D is a schematic of an embodiment of the invention Ti—Nb—Zr pacemaker leads.

One of these designs is shown in schematic form in FIGS. 14A and B. The pacemaker lead body 150 has a centrally disposed metallic conductor 152 typically made of cobalt-nickel alloy, such as MP35N®. This conductor 152 is usually made up of several strands of wire, each having a diameter of about 0.15-0.20 mm. The conductor 152 is covered by an insulative, protective polymer sheath 153 so that the elongate body 150 of the pacemaker lead has an overall diameter ranging from about 2.2 to about 3 mm. The pacemaker has a first end 154 with an electrode 158 for connecting to a pulse generator and a second end 156 with an electrode 157 for contacting heart muscle. An alternative embodiment is shown in FIG. 14C. As supplied, these two ends are covered with protective polyurethane caps which can be removed for installation of the pacemaker. In order to prevent electrical interference with the conductor 152, a polymeric insulative sleeve 153 is disposed over the entire pacemaker lead body 150, with the exception of the exposed electrodes 157 for contacting heart muscle and the contact electrode 158 for engaging with the pulse generator that houses the electronics and power pack for the pacemaker. As explained before, the organic polymeric sheath compositions, typically polyurethane, can slowly degenerate in the body causing problems, not only due to potential deterioration of electrical insulation and interference with electrical signals but also because of potentially toxic products of degradation.

The invention provides, as shown in FIG. 14C, a pacemaker wherein the conductor 152 is fabricated from a Ti—Nb—Zr alloy that is coated with a tightly adherent, low friction, bio- and hemocompatible coating, with the exception of the electrode for contacting heart muscle 157, and the electrode 158 at the other end of the lead for engaging the pulse generator. The coatings can be formed by in situ oxidation or nitriding of the Ti—Nb—Zr to produce an electrically insulative surface layer of from about 0.1 to about 3 microns in thickness, preferably less than about 0.5 microns in thickness. This process can be carried out at the same time the material is age-hardened. Alternatively, an insulative inert ceramic coating can be applied by conventional CVD or PVD methods either on the original Ti—Nb—Zr alloy surface or onto the diffusion hardened Ti—Nb—Zr surface. For these overlay coatings, the thickness can be as great as 20 microns. The overlay coatings include ceramic metal oxides, metal nitrides, metal carbides, amorphous diamond-like carbon, as detailed above. The electrical signal conductor 152 can comprise either a single wire or multiple wires. Exposed Ti—Nb—Zr metallic ends of the wire or wires are preferably connected directly to a pulse generator thereby avoiding the necessity for a weld or crimp to attach an electrode to the conductor which may result in local galvanic corrosion or physically weakened regions. Further, since the coatings provide a natural protective insulative surface, the use of a coiled construct could be avoided by using only a preferred single-strand, non-coiled low modulus Ti—Nb—Zr metallic wire construct for the conductor 152. This will also eliminate the need for stiff guide wire. Finally, the overall diameter of the pacemaker lead body 150 could be reduced considerably from the range of about 2.2-3 mm for current commercially available leads to about 0.2-1 mm. Optionally, the leads of the invention may be covered with a polymeric sheath.

Stents

Figure 11A:
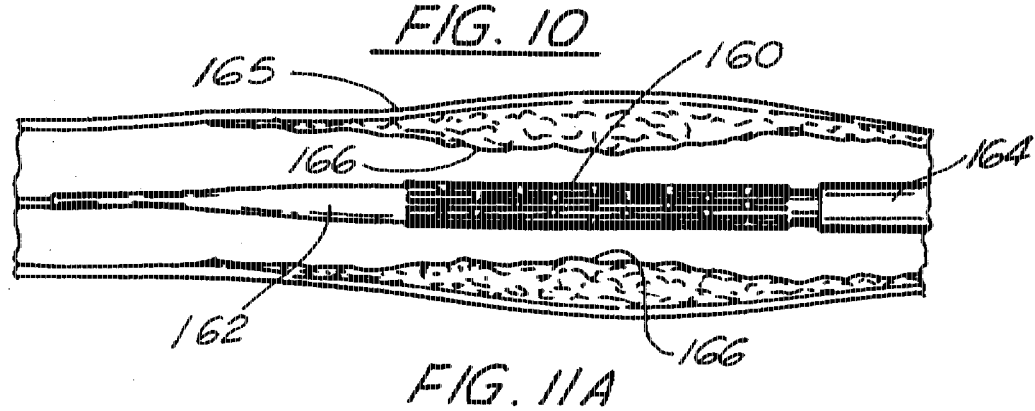
FIG. 11A is a schematic diagram showing a balloon expandable stent positioned within a segment of a blood vessel to be propped open.
Figure 11B:
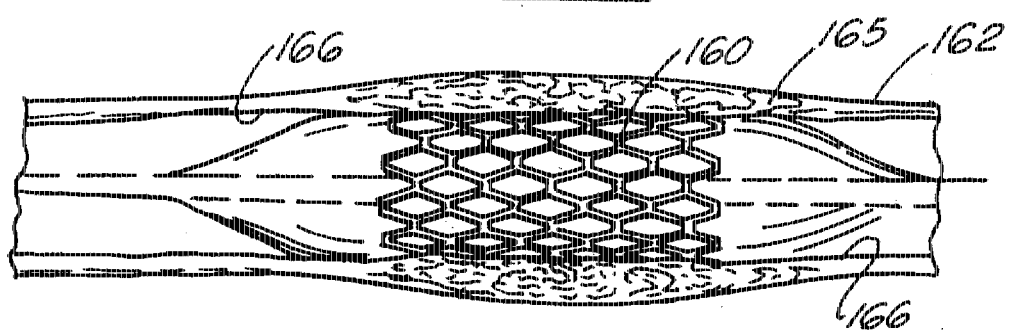
FIG. 11B is a schematic diagram showing a balloon expanding a stent into position within a blood vessel.
Figure 11C:
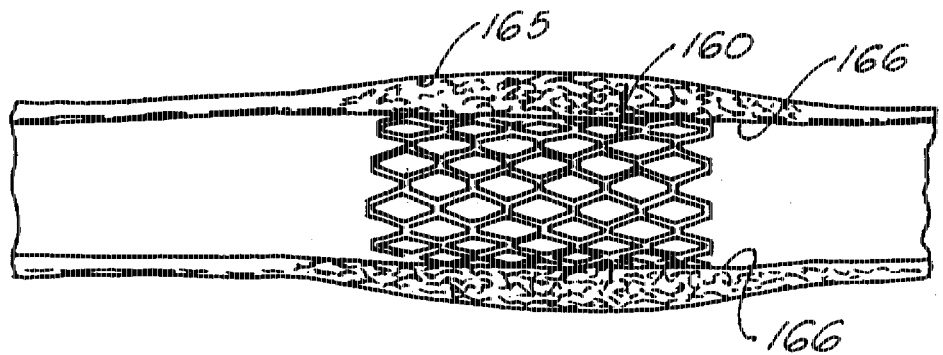
FIG. 11C is a schematic diagram of a stent expanded in a blood vessel.

FIG. 11A shows a schematic of an expandable stent 160, in non-expanded state, positioned on the distal end of a balloon expandable segment 162 of a guide wire 164. The stent is fabricated from Ti----Nb----Zr alloy and is designed so that it can be collapsed over a balloon segment of a balloon catheter. When the stent is in position, within segment of a tubular conduit 165 in the body, a blood vessel for example, to be propped open, the balloon 162 is expanded thereby expanding the stent 160 radially outward up to the blood vessel wall 166 so that means for gripping soft tissue, such as barbs (not shown), on the outer surface of the stent 160 engage and grip blood vessel tissue to anchor the stent 160 in position as shown in FIG. 11B. The balloon 162 is then collapsed and removed leaving the stent in place as shown in FIG. 11C. In this way, the blood vessel is permanently propped open. Urinary, gastrointestinal, and other stent applications are also provided using Ti----Nb----Zr alloy.

Grafts

Figure 10:
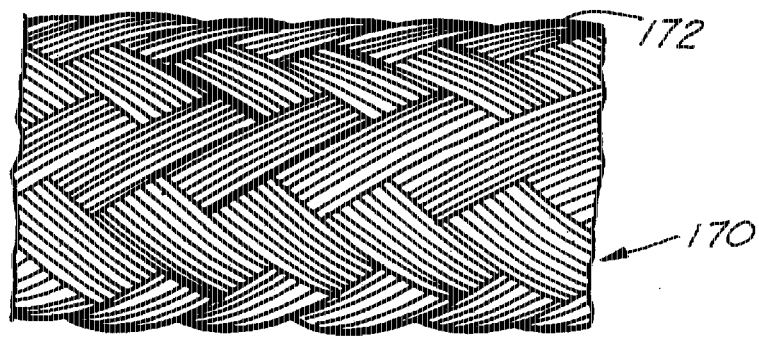
FIG. 10 is a schematic diagram of a vascular graft of woven metallic wire composition.

FIG. 10 is a representative sketch of a side view of a substantially tubular vascular graft 170 sized to graft onto a blood vessel and made of woven low modulus Ti----Nb----Zr wires 172. While the graft shown is made of woven wires of Ti----Nb----Zr, the graft can also be fabricated from a cylindrical tubing of this alloy. The graft can be fabricated from Ti----Nb----Zr alloy in the lower modulus cold worked condition, or in the slightly higher modulus aged condition with optional surface hardening. Additionally, protein, antibiotic, anti-thrombic, and other surface treatments may be employed to further improve the biocompatibility and clinical performance.

Defibrillators

FIGS. 12A and B show a defibrillator including a flexible silicone polymeric patch 300 with a coil of conductive wire 320 (typically titanium, stainless steel, or cobalt-nickel-chromium) on the side of the silicone patch 300 that will contact muscle tissue. When in place in the body, the lead wire 320 that carries power to the coil 340 extends out of the body (through the skin) and is electrically connected to a power source contained in a protective container 360. According to the invention, the lead wire 320 is fabricated with an electrically conductive core 350 of Ti----Nb----Zr alloy and is coated with an adherent electrically insulative coating 380, such as metal oxides, carbides, or nitrides, or with amorphous diamond-like carbon as shown in exaggerated detail FIG. 12B. This coating electrically insulates the lead wire from electrical contact with surrounding body tissue while also protecting the metallic core from corrosion and attack by body fluids, as described previously for the pacemaker lead. Elimination of the polymer coating results in the elimination of potentially toxic products of gradual degradation of the polymer and also the consequent shorting the system when the insulative coating is breached.

The Hardened Surfaces

The oxygen or nitrogen diffusion hardened surface of the alloy implants may be highly polished to a mirror finish to further improve blood flow characteristics. Further, the oxide- or nitride-coated surfaces maybe coated with substances that enhance biocompatibility and performance. For example, a coating of phosphatidyl choline, heparin, or other proteins to reduce platelet adhesion to the surfaces of the implant, or the use of antibiotic coatings to minimize the potential for infection. Boronated or silver-doped hardened surface layers on the implant reduces friction and wear between contacting parts of heart valves, prosthetic artificial hearts, ventricular assist devices, and other contacting parts in the invention cardiovascular implants. Additionally, amorphous diamond-like carbon, pyrolytic carbon, or other hard ceramic surface layers can also be coated onto the diffusion hardened surface to optimize other friction and wear aspects. The preferred diffusion hardened surface layer described in this application provides a hard, well-attached layer to which these additional hard coatings can be applied with a closer match between substrate and coating with respect to hardness. Other, conventional methods of oxygen surface hardening are also useful. Nitriding of the substrate leads to a hardened nitride surface layer. Methods of nitridation known in the art may be used to achieve a hard nitride layer.

Regardless of how a Ti----Nb----Zr alloy implant's surface is hardened, the friction and wear (tribiological) aspects of the surface can be further improved by employing the use of silver doping or boronation techniques. Ion-beam-assisted deposition of silver films onto ceramic surfaces can improve tribiological behavior. The deposition of up to about 3 microns thick silver films can be performed at room temperature in a vacuum chamber equipped with an electron-beam hard silver evaporation source. A mixture of argon and oxygen gas is fed through the ion source to create an ion flux. One set of acceptable silver deposition parameters consists of an acceleration voltage of 1 kev with an ion current density of 25 microamps per $cm^2$. The silver film can be completely deposited by this ion bombardment or formed partially via bombardment while the remaining thickness is achieved by vacuum evaporation. Ion bombardment improves the attachment of the silver film to the Ti----Nb----Zr alloy substrate. Similar deposition of silver films on existing metal cardiovascular implants may also be performed to improve tribiological behavior, as well as antibacterial response.

An alternate method to further improve the tribiological behavior of Ti----Nb----Zr alloy surfaces of cardiovascular implants is to apply boronation treatments to these surfaces such as commercial available boride vapor deposition, boron ion implantation or sputter deposition using standard ion implantation and evaporation methods, or form a boron-type coating spontaneously in air. Boric Acid ($H_3BO_3$) surface films provide a self-replenishing solid lubricant which can further reduce the friction and wear of the ceramic substrate. These films form from the reaction of the $B_2O_3$ surface (deposited by various conventional methods) on the metal surface with water in the body to form lubricous boric acid. Conventional methods that can be used to deposit either a boron (B), $H_3BO_3$, or $B_2O_3$ surface layer on the cardiovascular implant surface include vacuum evaporation (with or without ion bombardment) or simple oven curing of a thin layer over the implant surface. The self-lubricating mechanism of $H_3BO_3$ is governed by its unique layered,-triclinic crystal structure which allows sheets of atoms to easily slide over each other during articulation, thus minimizing substrate wear and friction.

Additionally, surfaces (metal or coated) of all the cardiovascular and medical implants discussed may optionally be coated with agents to further improve biological response. These agents include anticoagulants, proteins, antimicrobial agents, antibiotics, and the like medicaments.

Although the invention has been described with reference to its preferred embodiments, those of ordinary skill in the art may, upon reading this disclosure, appreciate changes and modifications which may be made and which do not depart from the scope and spirit of the invention as described above and claimed below.

What is claimed is:

1. A woven vascular graft for grafting onto a blood vessel, the woven vascular graft having enhanced hemocompatibility, comprising:
 a woven vascular graft at least partially fabricated from a metal alloy comprising:
  (i) titanium; and
  (ii) from about a range of 10 to about 20 wt. % niobium or from about 35 to about 50 wt. % niobium;
 wherein the alloy is free of deliberately added toxic elements, except such amounts of said toxic elements as may occur as impurities in the alloy and as contaminants as a result of an alloying process.

2. The woven vascular graft of claim 1, wherein said alloy further comprises an amount of zirconium from about 0.5 to about 20 wt. % zirconium which is sufficient to retard the transformation of β-phase titanium.

3. The woven vascular graft of claim 2, wherein the metal alloy comprises from about 0.5 to about 20 wt. % zirconium.

4. The woven vascular graft of claim 1, further comprising a hard outer surface layer on at least a portion of the woven vascular graft, said layer formed on the woven vascular graft by a process selected from the group consisting of oxygen diffusion hardening, nitrogen diffusion hardening, physical vapor deposition, and chemical vapor deposition.

5. The woven vascular graft of claim 2, further comprising a hardened outer surface layer on at least a portion of the woven vascular graft, said layer formed on the woven vascular graft by a process selected from the group consisting of oxygen diffusion hardening, nitrogen diffusion hardening, physical vapor deposition, and chemical vapor deposition.

6. The woven vascular graft of claim 1 or claim 2 or claim 3 or claim 4, wherein surfaces of the woven vascular graft that come into contact with body tissue or fluid are at least partially coated with a composition selected from the group consisting of anticoagulants, antimicrobial agents, antibiotics, and medicaments.

7. The woven vascular graft of claim 1 or claim 2 or claim 3 or claim 4, further comprising a lower friction wear-resistant outer surface layer on at least a portion of the woven vascular graft, said lower friction wear-resistant outer surface layer produced by a process selected from the group consisting of boronation and silver doping.

8. The woven vascular graft of claim 2, wherein the metal alloy comprises about 74 wt. % titanium, about 13 wt. % niobium, and about 13 wt. % zirconium.

9. The woven vascular graft of claim 2, wherein the metal alloy comprises titanium, from about 10 to about 20 wt. % niobium, and up to about 20 wt. % zirconium.

10. The woven vascular graft of claim 2, wherein the metal alloy comprises titanium, from about 35 to about 50 wt. % niobium, and up to about 20 wt. % zirconium.

11. A woven vascular graft for grafting onto a blood vessel, the woven vascular graft having enhanced hemocompatibility, comprising:
 a woven vascular graft at least partially fabricated from a metal alloy comprising:
  (i) titanium; and
  (ii) niobium and tantalum, wherein the combined wt. % of niobium and tantalum is from a range of about 10 to about 20 wt. % or from about 35 to about 50 wt. %;
 wherein the alloy is free of deliberately added toxic elements, except such amounts of said toxic elements as may occur as impurities in the alloy and as contaminants as a result of an alloying process.

12. The woven vascular graft of claim 11, wherein said alloy further comprises an amount of zirconium from about 0.5 to about 20 wt. % zirconium which is sufficient to retard the transformation of β-phase titanium.

13. The woven vascular graft of claim 12, wherein the metal alloy comprises from about 0.5 to about 20 wt. % zirconium.

14. The woven vascular graft of claim 11, further comprising a hardened outer surface layer on at least a portion of the woven vascular graft, said layer formed on the woven vascular graft by a process selected from the group consisting of oxygen diffusion hardening, nitrogen diffusion hardening, physical vapor deposition, and chemical vapor deposition.

15. The woven vascular graft of claim 12, further comprising a hard outer surface layer on at least a portion of the woven vascular graft, said layer formed on the woven vascular graft by a process selected from the group consisting of oxygen diffusion hardening, nitrogen diffusion hardening, physical vapor deposition, and chemical vapor deposition.

16. The woven vascular graft of claim 11 or claim 12 or claim 13 or claim 14, wherein surfaces of the woven vascular graft that come into contact with body tissue or fluid are at least partially coated with a composition selected from the group consisting of anticoagulants, antimicrobial agents, antibiotics, and medicaments.

17. The woven vascular graft of claim 11 or claim 12 or claim 13 or claim 14, further comprising a low friction wear-resistant outer surface layer on at least a portion of the woven vascular graft, said lower friction wear-resistant outer surface layer produced by a process selected from the group consisting of boronation and silver doping.

* * * * *